United States Patent
Liang et al.

(10) Patent No.: US 8,598,191 B2
(45) Date of Patent: Dec. 3, 2013

(54) CONTROLLED RELEASE COMPOSITIONS OF GAMMA-HYDROXYBUTYRATE

(75) Inventors: Likan Liang, Boyds, MD (US); Niraj Shah, Owings Mills, MD (US); Padmanabh P. Bhatt, Rockville, MD (US); Scott Ibrahim, Owings Mills, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

(21) Appl. No.: 13/476,369

(22) Filed: May 21, 2012

(65) Prior Publication Data

US 2012/0231085 A1  Sep. 13, 2012

Related U.S. Application Data

(63) Continuation of application No. 11/239,638, filed on Sep. 30, 2005, now Pat. No. 8,193,211.

(60) Provisional application No. 60/614,622, filed on Sep. 30, 2004.

(51) Int. Cl.
*A61K 9/20* (2006.01)
*A61K 9/24* (2006.01)
*A61K 9/28* (2006.01)

(52) U.S. Cl.
USPC ........... 514/289; 424/439; 424/464; 424/472; 424/474

(58) Field of Classification Search
None
See application file for complete search history.

(56) References Cited

U.S. PATENT DOCUMENTS

| | | | |
|---|---|---|---|
| 5,426,120 A | 6/1995 | Crepaldi et al. | |
| 5,594,030 A | 1/1997 | Conte et al. | |
| 5,840,331 A * | 11/1998 | Van Cauter et al. | 424/464 |
| 6,107,499 A | 8/2000 | Shashoua | |
| 7,015,200 B2 * | 3/2006 | Mamelak et al. | 514/23 |
| 7,374,779 B2 * | 5/2008 | Chen et al. | 424/451 |
| 2004/0121420 A1 | 6/2004 | Smith | |
| 2005/0220873 A1 * | 10/2005 | Han et al. | 424/468 |

OTHER PUBLICATIONS

Fishbein et al., "γ-Hydroxybutyrate in Mammalian Brain," The Journal of Biological Chemistry, Jan. 1964, 239(1):357-361.
Mamelak, Mortimer, "Gammahydroxybutyrate: An Endogenous Regulator of Energy Metabolism," Neuroscience & Biobehavioral Reviews, 1989, 13:187-198.
Nelson et al., "The Extraneural Distribution of γ-Hydroxybutyrate," Journal of Neurochemistry, Nov. 1981, 37(5):1345-1348.
Palatini et al., "Dose-dependent absorption and elimination of gamma-hydroxybutyric acid in healthy volunteers," Eur. J. Clin. Pharmacol., 1993, 45:353-356.

* cited by examiner

*Primary Examiner* — Susan Tran
(74) *Attorney, Agent, or Firm* — Foley & Lardner LLP; Stephen B. Maebius; Sunit Talapatra

(57) ABSTRACT

The present invention is directed to oral pulse-release pharmaceutical dosage form containing an immediate release component of gamma-hydroxybutyric acid, and one or more delayed/controlled release components of gamma-hydroxybutyric acid.

15 Claims, 7 Drawing Sheets

Figure 4. Dissolution profile of an immediate release core at pH 1.1

Figure 5. Dissolution profile of an Opadry AMB-coated immediate release core at pH 1.1

Figure 6. Dissolution profile of an EC-coated immediate release core at pH 1.1

CONTROLLED RELEASE COMPOSITIONS OF GAMMA-HYDROXYBUTYRATE

CROSS-REFERENCE TO RELATED APPLICATIONS

This application is a Continuation of U.S. application Ser. No. 11/239,638, filed Sep. 30, 2005, which claims priority to U.S. Provisional Application No. 60/614,622, filed Sep. 30, 2004, the entire contents of which are incorporated herein by reference.

FIELD OF THE INVENTION

The present invention is directed to pulse-released formulations of oxybate, or gamma-hydroxybutyric acid, salts, which reduce the number of dosages typically required for treatment. For instance, in the treatment of narcolepsy, a twice-nightly dosage regimen can be reduced to a single dose with the compositions of the present invention.

BACKGROUND OF THE INVENTION

Sodium gamma-hydroxybutyrate (GHB or sodium oxybate) is a naturally occurring metabolite of many mammalian tissues (Fishbein et al, J. Biol Chem. 239:357-61 (1964), Mamelak, Neurosci Biobehav Rev. 13(4):187-98 (1989), Nelson et al, J. Neurochem., 37:1345-48 (1981)) and has broad indications including narcolepsy, cataplexy, sleep paralysis, alcoholism, chronic schizophrenia, catatonic schizophrenia, atypical psychoses, chronic brain syndrome, neurosis, drug addiction and withdrawal, Parkinson's disease and other neuropharmacological illnesses, hypertension, ischemia, circulatory collapse, radiation exposure, cancer, myocardial infarction, anesthesia induction, sedation, growth hormone production, heightened sexual desire, anorectic effects, euphoria, smooth muscle relaxation, muscle mass production, and sleep.

Currently, sodium gamma-hydroxybutyrate is prescribed for patients with narcolepsy (Xyrem®, Orphan Medical) as a twice-nightly solution. Patients take an initial dose of sodium gamma-hydroxybutyrate around bedtime and must wake up four hours later to take a second dose. Such a dose regimen is rather inconvenient.

Other dosage forms of sodium gamma-hydroxybutyrate have also been disclosed. For example, U.S. Pat. No. 5,594,030 discloses controlled release pharmaceutical compositions of gamma hydroxybutyric acid salts consisting of a nucleus in the form of granulates or tablets which comprises GHB and a cellulosic matrix, wherein the drug substance is released within 7 to 8 hours.

Sodium gamma-hydroxybutyrate is highly soluble, hygroscopic, and strongly alkaline, and the therapeutic dose is normally very high. For example, a daily dose of 4.5 to 9 grams of Xyrem® is prescribed to narcolepsy patients. These characteristics of sodium gamma-hydroxybutyrate have some significant effects on coated particles or tablets comprising GHB. The high solubility of sodium gamma-hydroxybutyrate likely leads to drug migration into the coating layer during the coating process, and dissolves rapidly when the coated articles encounter water or bodily fluids, creating "pores" that allow leakage of the drug from the coated articles. Further, when sodium gamma-hydroxybutyrate penetrates/diffuses into the coating film, it may interfere with the coating material itself. For example, penetrated/diffused sodium gamma-hydroxybutyrate may act as a strong base which reacts with pH sensitive coating polymers, such as Eudragit L30-D55 for instance, weakening the coating layer and lowering the coating efficiency.

Further, the absorption of sodium gamma-hydroxybutyrate seems to be capacity-limited (Palatini et al, Eur. J Clin Pharmacol. (1993) 45:353-356), but it has been unclear whether the absorption of this drug is region-specific, which would affect the oral delivery of GHB.

Therefore, a need exists in the art for a more convenient dosing regimen, an effective dosage form of controlled release of gamma-hydroxybutyric acid salts and an efficient way to deliver gamma-hydroxybutyric acid salts to an animal in the gastrointestinal tract. The current invention satisfies these needs.

SUMMARY OF THE INVENTION

It is an object of the present invention to provide a convenient and effective dosage form of GHB, whereby the number of dosages can be reduced.

It is another object of the present invention to provide compositions of GHB that have a reduced likelihood of drug migration from the dosage form.

The present invention takes into account the surprising discovery by the present inventors that the oral absorption of sodium gamma-hydroxybutyrate is region specific in animals, and that the absorption is higher in the upper GI tract than in the lower GI tract.

The present invention is also directed to methods and compositions for the targeting of the upper GI tract of an animal for improved absorption of sodium gamma-hydroxybutyrate.

The current invention provides methods and compositions for convenient administration of multiple doses of one or more gamma-hydroxybutyric acid salts to an animal. It provides a convenient once nightly or once daily dose regiment for the oral delivery of one or more gamma-hydroxybutyric acid salts to an animal. With the compositions of the present invention, a patient does not need to wake up at night to take a second dose then go back to sleep.

The current invention also provides methods and compositions for the effective delayed/controlled release of multiple (i.e., more than one) doses of one or more gamma-hydroxybutyric acid salts. The current invention provides methods and compositions to improve the gastro-stability of delayed/controlled release particulates (e.g. beads, granules, minitabs or pellets) containing gamma-hydroxybutyric acid salts.

The current invention further provides methods and compositions for the effective delivery of multiple doses of gamma-hydroxybutyric acid salts to one or more specific regions in the gastrointestinal tract of an animal. It provides methods and compositions for the targeting of the upper GI tract of an animal to improve the effectiveness of the absorption of gamma-hydroxybutyric acid salts from the delayed/controlled release particles.

DETAILED DESCRIPTION OF THE INVENTION

Figure 1:
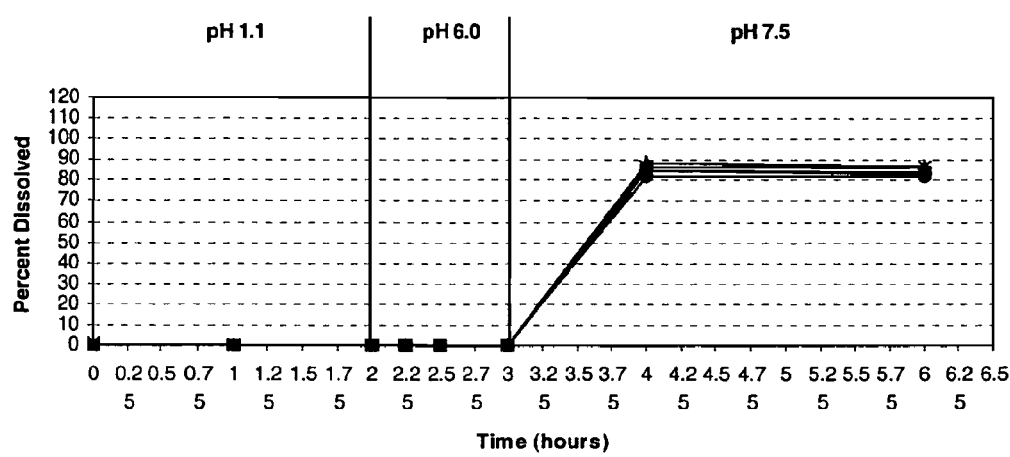
FIG. 1. Dissolution profile of a colon-targeting delayed release prototype with a neutralizing agent in the barrier coat.

The current invention provides methods and compositions for convenient administration of multiple (i.e. more than one, "pulsed") doses of one or more gamma-hydroxybutyric acid salts to an animal.

It also provides methods and compositions for the effective delayed/controlled release of multiple doses of one or more gamma-hydroxybutyric acid salts.

The current invention provides methods and compositions to improve the gastro-stability of the delayed/controlled release particles containing gamma-hydroxybutyric acid salts.

The current invention further provides methods and compositions for the effective delivery of multiple doses of gamma-hydroxybutyric acid salts to one or more specific regions in the gastrointestinal tract of an animal for effective absorption.

Specifically, at the essence of the present invention is a dosage form comprising one or more pH sensitive delayed/controlled release particles (e.g. beads, granules, minitabs or pellets), wherein each of the pH sensitive delayed/controlled release particles is composed of an immediate release core comprising one or more gamma-hydroxybutyric acid salts and one or more pharmaceutically acceptable excipients, one or more barrier coats surrounding such core (with or without a neutralizing agent), a pH sensitive enteric release coat around said barrier coat, and optionally an overcoat.

The dosage forms of the current invention comprise an immediate release component in the form of a solid, a semi-solid or a liquid, comprising one or more gamma-hydroxybutyric acid salts and optionally one or more pharmaceutically acceptable excipients, wherein the immediate release component is present together with (or separated contained from) one or more pH sensitive delayed/controlled release particles.

The dosage forms thus provide, which administered together or sequentially, multiple release pulses of gamma-hydroxybutyric acid salts targeting multiple regions in the gastrointestinal tract of an animal for improved absorption.

In one of the preferred embodiments, the composition comprises multiple delayed release pellets or beads (used interchangeably herein) and an immediate release component. In a most preferred embodiment, the dosage form comprises a liquid immediate release component, and two delayed/controlled release pellets/beads.

Each of the pH sensitive delayed/controlled release particles in the current invention is designed to release its contents at a specific region in the gastrointestinal tract of an animal. The one or more pH sensitive delayed/controlled release particles releases the contents at one or more corresponding regions in the gastrointestinal tract of an animal.

The immediate release component, in the form of a solid, a semi-solid or a liquid, of the current invention releases its contents immediately for absorption upon oral administration. Preferably, due to the high dosage of GHB, the immediate release component is a liquid.

Combining the immediate release component and one or more pH sensitive delayed/controlled release particles of the current invention can constitute a complete once-nightly or once-daily dose. The term "combining" as used herein means supplying and consuming all components (1) simultaneously in the same presentation or dosage form, or (2) simultaneously in different presentations or dosage forms, or (3) sequentially in the same presentation or dosage forms, or (4) sequentially in different presentations or dosage forms.

For example, an immediate release component in the form of particles and one or more pH sensitive delayed/controlled release particles are supplied as pre-mixed doses, and are consumed simultaneously at the time of dosing. Or, an immediate release component in the form of particles and one or more pH sensitive delayed/controlled release particles are supplied in separated parts, and are consumed simultaneously at the time of dosing. Alternatively, an immediate release component in the form of a powder and one or more pH sensitive delayed/controlled release particles are supplied in separate parts, and are consumed simultaneously at the time of dosing. In another embodiment, an immediate release component in the form of a solution and one or more pH sensitive delayed/controlled release particles are supplied in separate parts, and are consumed simultaneously at the time of dosing. Or, an immediate release component in the form of a solution and one or more pH sensitive delayed/controlled release particles are supplied in separated parts, and are consumed sequentially at the time of dosing. Other permutations would be apparent in those skilled in the art.

In one embodiment of the present invention, the delayed/controlled release component(s) is/are administered prior to the immediate release component, which can be administered from several minutes to about a half hour or more later (for practical reason, likely no more than about an hour later because the patient will become somewhat sleepy from the first dose). Thus, in it's most basic form, the present invention is directed to the delayed/controlled release component(s), which have utility as a separately administrable dosage form. These components can be supplied as a separate entity, and preferable used in conjunction with an immediate release dosage form as is currently marketed.

Multiple (i.e. more than one) delayed releases can be achieved by combining multiple pH sensitive delayed/controlled release particles targeting certain sites of the GI tract of an animal. For example, an immediate release component can be combined with two pH sensitive delayed/controlled release particles that are released at two different sites in the GI tract to provide an immediate release and two other delayed release pulses.

An immediate release component can be combined with one type of pH sensitive delayed/controlled release particles to provide two pulses of gamma-hydroxybutyric acid salts, which can conveniently replace the nightly multi-dose regimen of the existing commercial product. In this case, a patient does not need to wake up and take a second dose during the night, as described earlier.

Preferably, an immediate release component is combined with one or more pH sensitive delayed/controlled release particles to provide multiple releases in a period of time. Preferably, an immediate release component is combined with one or more pH sensitive delayed/controlled release particles targeted to the upper GI tract of an animal. The inventors discovered that the absorption of sodium gamma-hydroxybutyrate in the GI tract of an animal is site specific, and that the absorption of sodium gamma-hydroxybutyrate in the upper GI tract is higher than in the lower GI tract. The aforementioned combination therefore provides an initial dose and one or more delayed doses of gamma-hydroxybutyric acid salts, thereby providing an effective and convenient dose regimen for treating a patient.

More preferably, an immediate release component is combined with a single type of pH sensitive delayed/controlled release particles targeted to the duodenum or the jejunum of an animal to provide a two-pulse regiment to treat a patient.

The dose ratio of the immediate release component to one or more pH sensitive delayed/controlled release particles is dictated by the type of therapy and readily determined by the clinician, using currently available dosages as a reference. For example, the immediate release dose can be equivalent of, higher than, or lower than, the one or more delayed release doses.

It is contemplated that the delayed release dose amount, which is used to replace the second nightly dose (currently as a solution) in the current treatment of narcolepsy patients, can be the same as the immediate release dose amount, although the bioavailability is lower further along the GI tract, or even at a reduced dose amount, since the patients do not need to wake up and take a separate second nightly dose then go back to sleep.

It is also contemplated that the immediate release component can be at a slightly higher than normal dose, and the delayed release dose can be at a normal dose or at a reduced dose.

It is also contemplated that an immediate release component can be combined with one or more pH sensitive delayed/controlled release particles that are at reduced doses. For example, an immediate release dose can be combined with 0.7 equivalent dose of a duodenum-targeting delayed release component and 0.2 equivalent dose of a colon-targeting delayed release component to give a broader time coverage.

The immediate release component and one or more pH sensitive delayed/controlled release particles of the current invention can be administered to an animal directly, or mixed/sprinkled with fluids, soft foods (i.e. yogurt, applesauce), or pharmaceutically acceptable carriers. For example, an immediate release component in the form of a solution can be mixed with juice and the pH sensitive delayed/controlled release particles can be combined with foods (such as yogurts) for administration. Or, an immediate release component in the form of particles and the pH sensitive delayed/controlled release particles can be sprinkled with drinkable yogurt for dosing.

The Immediate Release Component

The dosage forms of the current invention comprise an immediate release component in the form of a solid, a semi-solid or a liquid. It can be a particle, a bead, a pellet, a granulate, a powder, a tablet, a minitablet, a capsule, a caplet, a lozenge, a hard shell or soft shell capsule, a sachet, a cachet, a solid dispersion, a solid solution, a suspension, an emulsion, a lotion, a solution, a liquid drop, an elixir, a syrup, a tincture, a liquid spray, an aerosol, a gel, an ointment, a cream, or the like.

The immediate release component can be present together with one or more of the pH sensitive delayed/controlled release particles described herein, or separated from the pH sensitive delayed/controlled release particles.

For example, the immediate release component can be in the form of particles that are pre-mixed with the pH sensitive delayed/controlled release particles. Or the two components can be provided as separate parts, possibly in a kit, wherein both components can be consumed together, or separately in a sequential manner.

In another example, the immediate release component can be in the form of a powder that is pre-mixed with the pH sensitive delayed/controlled release particles prior to ingestion. In this embodiment, the immediate release component is a powder comprising up to 100% of one or more gamma-hydroxybutyric acid salts and optionally one or more pharmaceutically acceptable excipients. Such a powder can be taken as is, or preferably is stirred into a drink or food along with the delayed/controlled release beads/pellets/minitabs.

In another preferred embodiment, the immediate release component is an aqueous solution (like the current Xyrem® product) of one or more gamma-hydroxybutyric acid salts stabilized with antioxidants, stabilizers, preservatives and neutralizing agents.

In yet another example, which is preferred because of the very high dosage needed for this drug, the immediate release component can be in the form of a solution that is provided separately from the pH sensitive delayed/controlled release particles, possibly in a kit form. The immediate release component is an aqueous solution (like the current Xyrem® product) of one or more gamma-hydroxybutyric acid salts stabilized with antioxidants, stabilizers, preservatives and neutralizing agents. Preferably, the delayed release particles are mixed with the liquid and then ingested.

The immediate release component of the current invention comprises one or more gamma-hydroxybutyric acid salts and optionally one or more pharmaceutically acceptable excipients, wherein the gamma-hydroxybutyric acid salts are selected from gamma-hydroxybutyric acid sodium salt, gamma-hydroxybutyric acid potassium salt, gamma-hydroxybutyric acid tetraammonium salt, or any other pharmaceutically acceptable salt forms of gamma-hydroxybutyric acid.

The immediate release component comprises from about 20% to about 100% by weight of one or more gamma-hydroxybutyric acid salts and optionally one or more pharmaceutically acceptable excipients.

The pharmaceutically acceptable excipients in the immediate release component are those known in the art as suitable for use in solid, semi-solid or liquid dosage forms, including but not limited to, binders, lubricants, anti-adherents, glidants, granulating aids, fillers, disintegrants, antioxidants, stabilizers, preservatives, neutralizing agents, buffering agents, tonicifiers, moisture absorbents, colorants, flavorants, sweeteners, sugars, and taste-masking agents, suspending agents, thickening agents, gelling agents, solvents, solubilizers, surfactants, absorption enhancers, emulsifying agents, and combinations thereof.

The total amount of these pharmaceutically acceptable excipients in the immediate release component is from about 0% to about 80% by weight.

Examples of these pharmaceutically acceptable excipients in the immediate release component of the current invention include, but are not limited to, binders/fillers: microcrystalline cellulose, silicified microcrystalline cellulose, polyvinylpyrrolidone, hydroxypropyl cellulose, starch, pregelatinized starch, starch paste, lactose, mannitol, sorbitol, xylitol, sucrose, calcium phosphate, calcium carbonate, ethylcellulose, methylcellulose, and Acacia; lubricants/anti-adherents/glidants/granulating aids: talc, sodium lauryl fumarate, fumed silicon dioxide, colloidal silica, titanium dioxide, kaolin, magnesium stearate, calcium stearate, stearic acid, hydrogenated vegetable oils, and sodium lauryl sulfate; disintegrants: sodium starch glycolate, croscarmellose sodium, cross-linked polyvinylpyrrolidone, and alginic acid; antioxidants/stabilizers/preservatives: riboflavin, tocopherol, vitamin E TPGS, BHT, BHA, cysteine and derivatives, ascorbates, sorbates, benzoates, propionates, bicarbonates, thiosulfates, metabisulfites, EDTA, carrageen, gums and benzyl alcohol; neutralizing agents: acids such as malic acid, citric acid, tartaric acid, ascorbic acid, oleic acid, capric acid, caprylic acid, benzoic acid, polyacids, acidic ionic resins, and other acidic excipients; suspending agents/thickening agents/ gelling agents: mineral oils, vegetable oils, silicon dioxide, various gums such as xanthan gum, locust bean gum, gum Arabic, alginates, Carbopols, polyvinyl alcohols, carrageenan, gelatin, starches; or mixtures thereof.

Preferably, if the immediate release component is a solid pellet, bead or minitablet or the like, that component is also used as the immediate release core of the pH sensitive delayed/controlled release particles by coating them using materials and methods similar to the barrier coats or the overcoat as described herein.

Delayed/Controlled Release Particles

The immediate release core of the pH sensitive delayed/ controlled release particles (i.e., beads, pellets, minitabs, granulate, etc.) of the current invention comprises from about 20% to about 99% of one or more gamma-hydroxybutyric acid salts by weight of the core and one or more pharmaceutically acceptable excipients, wherein the gamma-hydroxybutyric acid salts are selected from gamma-hydroxybutyric acid sodium salt, gamma-hydroxybutyric acid potassium salt, gamma-hydroxybutyric acid tetraammonium salt, or any other pharmaceutically acceptable salt forms of gamma-hydroxybutyric acid, or combinations thereof.

One or more pharmaceutically acceptable excipients in the immediate release core of the pH sensitive delayed/controlled release particles of the current invention are excipients known in the art as suitable for use in particulates, including but not limited to binders, lubricants, anti-adherents, glidants, granulating aids, fillers, disintegrants, antioxidants, stabilizers, preservatives, neutralizing agents, buffering agents, moisture absorbents, colorants, flavorants and task-masking agents.

The total amount of these pharmaceutically acceptable excipients in the immediate release core is from about 1% to about 80% by weight of the core.

Examples of these pharmaceutically acceptable excipients in the immediate release core of the current invention include, but are not limited to, binders/fillers: microcrystalline cellulose, silicified microcrystalline cellulose, polyvinylpyrrolidone, hydroxypropyl cellulose, starch, pregelatinized starch, starch paste, lactose, mannitol, sorbitol, xylitol, sucrose, calcium phosphate, calcium carbonate, ethylcellulose, methylcellulose, and Acacia; lubricants/anti-adherents/glidants/ granulating aids: talc, sodium lauryl fumarate, fumed silicon dioxide, colloidal silica, titanium dioxide, kaolin, magnesium stearate, calcium stearate, stearic acid, hydrogenated vegetable oils, and sodium lauryl sulfate; disintegrants: sodium starch glycolate, croscarmellose sodium, cross-linked polyvinylpyrrolidone, and alginic acid; antioxidants/stabilizers/ preservatives: riboflavin, tocopherol, vitamin E TPGS, BHT, BHA, cysteine and derivatives, ascorbates, sorbates, benzoates, propionates, bicarbonates, thiosulfates, metabisulfites, EDTA, carrageen, gums and benzyl alcohol; neutralizing agents: acids such as malic acid, citric acid, tartaric acid, ascorbic acid, oleic acid, capric acid, caprylic acid, benzoic acid, polyacids, acidic ionic resins, and other acidic excipients; or mixtures thereof.

Preferably, the immediate release core of the current invention comprises one or more excipients selected from binders, lubricants, anti-adherents, glidants and neutralizing agents.

The lubricants/anti-adherents/glidants may be selected from talc, sodium lauryl fumarate, fumed silicon dioxide, magnesium stearate and stearic acid, for instance. Preferably, the lubricants/anti-adherents/glidants are selected from one or both of talc and magnesium stearate.

In a preferred embodiment, the amount of talc in the immediate release core of the current invention about 1% to about 25% by weight of the core. More preferably, this amount is from about 5% to about 15% by weight of the core.

If magnesium stearate is used in the core it is present in an amount of from about 0% to about 10% by weight of the core. More preferably, this amount is from about 0.1% to about 5% by weight of the core.

Preferably, the binders/fillers in the immediate release core are selected from microcrystalline cellulose, silicified microcrystalline cellulose, polyvinylpyrrolidone, and hydroxypropyl cellulose.

Preferably, the immediate release core comprises microcrystalline cellulose or silicified microcrystalline cellulose at about 1% to about 80% by weight of the core. More preferably, the immediate release core comprises microcrystalline cellulose or silicified microcrystalline cellulose at about 3% to about 40% by weight of the core.

Preferably, the immediate release core comprises a neutralizing agent. The uptake of gamma-hydroxybutyric acid salts may be affected by the environmental pH and the ionization state of the salts. Preferably, the immediate release core contains a neutralizing agent to modulate the ionization state of the salt for better absorption in the gastrointestinal tract.

The immediate release cores in the pH sensitive delayed/ controlled release particles of the current invention are made by techniques and equipment known in the art, for example dry blending, milling, dry granulation, wet granulation, pelletization, direct pelletization, extrusion, melt-extrusion, spheronization, drug layering, compaction, compression. Solvents can be used to facilitate the preparation of the immediate release core. These solvents can be removed partially or completely during the preparation of the core. Suitable solvents include, but are not limited to, water, alcohols, ketones and combinations thereof. For example, water and/or alcohols can be used during wet granulation and spheronization, or during direct pelletization, or during drug layering, and the solvents can be removed thereafter.

Barrier Coat(s)

One or more barrier coats applied to the pH sensitive delayed/controlled release particles of the current invention provides a barrier, and a neutralization zone when a neutralizing agent is used, between the immediate release core and the enteric coat, and functions to prevent gamma-hydroxybutyric acid salts from entering into or interfering with the enteric coat. The barrier coats can optionally act also as a controlled release coat to control the rate of release of gamma-hydroxybutyric acid salts from the immediate release core.

The barrier coats in the current invention provide a barrier and optionally a neutralization zone between the immediate release core and the enteric coat to prevent the alkalinic gamma-hydroxybutyric acid salts from migrating into and interfering with the pH sensitive enteric coat. If the highly water-soluble and strongly alkalinic gamma-hydroxybutyric acid salts migrate into the enteric coat, they not only create channels in the enteric coat which act as pore formers, but also react with the functional groups of the coat materials and weaken the enteric coat. By controlling the thickness and/or the permeability of the barrier coats, the migration of gamma-hydroxybutyric acid salts can be minimized. Further, neutralizing agents, mainly acidifiers, can be used in the barrier coat to neutralize gamma-hydroxybutyric acid salts in the barrier layer thus preventing these alkalinic salts from reacting with the enteric coat material.

Moreover, the barrier coats can optionally act as a controlled release coat to control the rate of release of gamma-hydroxybutyric acid salts from the immediate release core, allowing for site specific and controlled release of gamma-hydroxybutyric acid salts in the GI tract of an animal.

Suitable coating materials for the barrier coats in the current invention include, but are not limited to, cellulosic polymers such as ethylcellulose, methylcellulose, hydroxypropyl cellulose, hydroxypropyl methylcellulose, cellulose acetate, cellulose acetate phthalate, polyvinyl alcohol, or other water-based or solvent-based coating materials.

Suitable neutralizing agents in the barrier coats of the current invention include, but are not limited to, acids such as malic acid, citric acid, tartaric acid, ascorbic acid, oleic acid, capric acid, caprylic acid, benzoic acid, polyacids (a polymer with multiple carboxylic acid functional groups or side chains, e.g. polymethacrylic acid, or molecules with multiple acid functional groups, e.g. EDTA, ethylenediaminetetraacetic acid), acidic ionic resins, and other acidic excipients, and are used in amounts sufficient to neutralize any migrating gamma-hydroxybutyric acid salts. Preferably, the amount of neutralizing agent in the barrier coat is at about 0.01% to about 10% mol/mol of the gamma-hydroxybutyric acid salts in the core. More preferably, this amount is at about 1% to about 5% mol/mol of the salts.

The barrier coats in the current invention can further comprise other additives known in the art, such as pore formers, plasticizers, anti-adherents, glidants, and antifoam agents. Pore formers suitable for use in the barrier coats of the invention are organic or inorganic agents, and include materials that can be dissolved, extracted or leached from the coating in the environment of use. Examples of the pore formers include, but are not limited to, organic compounds such as saccharides including sucrose, glucose, fructose, mannitol, mannose, galactose, sorbitol, pullulan, dextran; polymers soluble in the environment of use such as water-soluble hydrophilic polymers, hydroxyalkylcelluloses, carboxyalkylcelluloses, hydroxypropylmethylcellulose, cellulose ethers, acrylic resins, polyvinylpyrrolidone, cross-linked polyvinylpyrrolidone, polyethylene oxide, Carbowaxes, Carbopol, and the like, diols, polyols, polyhydric alcohols, polyalkylene glycols, polyethylene glycols, polypropylene glycols, or block polymers thereof, polyglycols, poly(a-w)alkylene-diols; inorganic compounds such as alkali metal salts, lithium carbonate, sodium chloride, sodium bromide, potassium chloride, potassium sulfate, potassium phosphate, sodium acetate, sodium citrate, suitable calcium salts, and the like. The amount of pore formers used in the barrier coats varies depending on the functions of the barrier coats. For example, if the pH sensitive delayed/controlled release particles are intended for immediate release after entering the targeted site in the GI tract, high amounts of pore formers (e.g. as high as about 50% by weight of the barrier coat) can be used. If the pH sensitive delayed/controlled release particles are for controlled release after entering the targeted site in the GI tract, little or no pore formers are used (e.g. no more than about 25% by weight of the barrier coat).

The rate of release of gamma-hydroxybutyric acid salts in the pH sensitive delayed/controlled release particles can also be controlled by varying the thickness and/or types of the barrier coats, with or without the use of pore formers. For example, when ethylcellulose is used together with PVP K30 (5%) as the pore former, or when ethylcellulose is used with or without a water-insoluble plasticizer and without the use of any pore formers, or when ethylcellulose is used with a water-soluble plasticizer such as triethyl citrate, the barrier coat can be between about % to about 20% weight gain on the particles in order to obtain different controlled release profiles. Or, when Opadry AMB is used as the barrier coat, the barrier coat can be from about 2% to about 10% weight gain on the particles, in order to obtain an immediate release profile.

The barrier coats can also be multiple coats of different coating materials. For example, the barrier coats can have an Opadry AMB initial barrier coat, and an ethylcellulose secondary barrier coat surrounding the initial coat, and optionally an Opadry tertiary barrier coat surrounding the secondary coat.

The barrier coats can be water-based coatings, or organic solvent-based coatings. Preferably, the barrier coat is organic solvent-based coating such as an alcohol or alcohol-water or ketone based coating.

Furthermore, the barrier coats of the current invention can provide moisture protection for hygroscopic gamma-hydroxybutyric acid salts inside the barrier coats.

The pH Sensitive Enteric Coat

The pH sensitive enteric release coat of the current invention enables targeted delivery of the particles to a specific region in the GI tract. It also provides a time delay in the release of the gamma-hydroxybutyric acid salts from the pH sensitive delayed/controlled release particles of the current invention. Combinations of more than one of these pH sensitive delayed/controlled release particles in a dosage form will provide multiple doses of gamma-hydroxybutyric acid salts delivered to multiple sites in the GI tract with multiple delay time periods or pulses. When combined with any controlled release characteristics of the barrier coats, the compositions of the current invention provide a wide spectrum of combined site specific, delayed and controlled release profiles for oral delivery of gamma-hydroxybutyric acid salts to an animal.

Materials suitable for use in the pH sensitive enteric coat of the current invention are pH sensitive coating materials known in the art. The pH sensitive coating materials include, but are not limited to, methacrylate-based coating materials such as polymers of methacrylic acid and methacrylates (e.g. Eudragit L 100-55, Eudragit L 30-D55, Eudragit L 100, Eudragit S 100, Eudragit FS 30 D), cellulose-based coating materials such as cellulose acetate phthalate, carboxymethyl ethylcellulose, cellulose acetate trimellitate, hydroxypropylmethylcellulose phthalate, hydroxypropylmethylcellulose acetate succinate, Shellac-based coating materials such as Emcoat 120N and Marcoat 125, and other enteric coating polymers such as polyvinyl acetate phthalate.

Other additives such as solvents, plasticizers (e.g. PEG, triethyl citrate, dibutyl secbate), anti-tack agents (e.g. talc), anti-foam agents, colorants, fillers/extenders, flavorants, surfactants (e.g. sodium lauryl sulfate), bases, buffers, and other suitable additives known in the art can also be used together with the pH sensitive enteric coating materials.

The coating can be organic solvent-based, or aqueous-based, or organic solvent/aqueous based.

Preferably, the pH sensitive delayed/controlled release particles are prepared by coating the barrier-coated immediate release core with an appropriate pH sensitive coating material targeting to a specific region in the GI tract of an animal. The weight gain of the pH sensitive enteric coating is from about 10% to about 70% of the final enteric-coated particle weight. Preferably, the weight gain of this coating is from about 20% to about 60% of the final enteric-coated particles. More preferably, the weight gain of this coating is about 30% to about 50% of the final enteric-coated particle weight.

The pH sensitive enteric release coat can target both the upper part and the lower part of the GI tract of an animal. The pH sensitive enteric coat releases/dissolves in one of the stomach, the duodenum, the jejunum, the ileum, or the colon of an animal. Suitable pH sensitive enteric coating materials targeting each of these regions in humans are known in the art, such as Eudragit E 100 or Eudragit E PO (stomach), Eudragit L 30 D-55 and Eudragit L 100-55 (duodenum), Eudragit L 12.5 and Eudragit L 100 (jejunum), Eudragit S 100 (ileum), and Eudragit FS 30 D (colon).

Preferably, the pH sensitive enteric release coat releases/dissolves in the upper GI tract of an animal, which will allow for better absorption of the drug. In a more preferred embodiment, the pH sensitive enteric coat releases/dissolves in the duodenum or the jejunum of an animal.

Optionally, acidifiers or bases can be added to the pH enteric coating materials to adjust the target release/dissolution pH or region in the GI tract of an animal. Further, acidifiers in the pH sensitive enteric coat can also counteract the alkaline effect from any migrating gamma-hydroxybutyric acid salts. Suitable acidifiers are organic acids or inorganic acids, acidic excipients, and the aforementioned neutralizing agents.

The delay in release of gamma-hydroxybutyric acid salts from the particles of the current invention can be achieved by selecting different pH sensitive enteric release coats targeting the desired regions of the GI tract of an animal. Combinations of various particles with different pH sensitive enteric coats thus provide multiple pulses of gamma-hydroxybutyric acid salts with various delayed release times.

Overcoats

Optionally, the immediate and/or delayed/controlled release solid dosage forms of the current invention can be coated with an overcoat. The overcoat can be a moisture barrier coat, a protection coat, a seal coat, a taste-masking coat, a flavor coat, a polish coat, a color coat, or any other cosmetic coats. Suitable coating materials for such an overcoat are known in the art, including, but are not limited to, cellulosic polymers such as hydroxypropylmethylcellulose, hydroxypropylcellulose, microcrystalline cellulose carrageenan, and ethylcellulose.

Other additives known in the art can also be used in the overcoat, such as solvents, plasticizers (e.g. PEG, triethyl citrate, dibutyl secbate), anti-tack agents (e.g. Talc), anti-foam agents, colorants, fillers/extenders, flavorants, and surfactants (e.g. sodium lauryl sulfate).

The invention now will be described with respect to the following examples; however, the scope of the present invention is not intended to be limited thereby.

EXAMPLES

Example 1

Compositions of the Immediate Release Core and/or the Immediate Release Component

TABLE 1

| Ingredients | PD0231-25 | PD0231-24A | PD0231-24B | PD0231-24C | PD0231-19 | PD0231-17A | PD0231-16 | PD0231-15A | P00231-12 | PD0231-10A |
|---|---|---|---|---|---|---|---|---|---|---|
| Sodium gamma-hydroxybutyrate | 80 | 80 | 84 | 80 | 80 | 80 | 80 | 90 | 40 | 80 |
| Avicel PH101 | 10 | 15 | 10 | 10 | 20 | 10 | 15 | 10 | 58 | — |
| Talc | 9 | 5 | 5 | 9 | — | — | — | — | — | — |
| Magnesium stearate | 1 | — | 1 | 1 | — | — | — | — | — | — |
| SMCC 50 | — | — | — | — | — | — | — | — | — | 15 |
| Emcompress | — | — | — | — | — | 10 | 5 | — | — | — |
| HPMC E5 | — | — | — | — | — | — | — | — | 2 | — |
| PVP K30 | — | — | — | — | — | — | — | — | — | 5 |
| Lactose | — | — | — | — | — | — | — | — | — | — |
| Water | 10* | 11.3* | 11.3* | 5.5* | 11.3* | 15* | 15* | 12* | 10.5* | 9* |
| Ethanol | — | — | — | — | — | — | — | — | — | 9* |

TABLE 2

| Ingredients | PD0231-10B | PD0231-10C | PD0231-9B | PD0231-8A |
|---|---|---|---|---|
| Sodium gamma-hydroxybutyrate | 70 | 65 | 80 | 83 |
| Avicel PH101 | — | — | — | — |
| Talc | — | — | — | — |
| Magnesium stearate | — | — | — | — |
| SMCC 50 | 28 | 35 | 17 | 17 |
| Emcompress | — | — | — | — |
| HPMC E5 | 2 | — | 1 | — |
| PVP K30 | — | — | — | — |
| Lactose | — | — | 2 | — |
| Water | 20* | 18* | 10.8 | 9.5 |
| Ethanol | — | — | — | — |

Number in parts by weight.
*Removed partially or completely during preparation

Example 2

Preparation of the Immediate Release Core

The immediate release core can be made by techniques or processes or equipments known in the art, including but are not limited to dry blending, milling, dry granulation, wet granulation, pelletization, direct pelletization, extrusion, melt-extrusion, spheronization, drug layering, as exemplified by the following preparations:

Dry powders of sodium gamma-hydroxybutyric acid, Avicel PH101, Talc and magnesium stearate were screened and mixed briefly, then charged into a high shear granulator. Water was added to the mixture during the granulation. The granulates were extruded through a screen with a desirable pore size then spheronized to yield pellets. The pellets were dried in an oven for a sufficient time, for example overnight, then screened.

Example 3

Moisture Protection Coat of the Immediate Release Core

Opadry AMB Coating Solution:

| | |
|---|---|
| Opadry AMB | 25 g |
| Deionized water | 475 g |

Uncoated pellets from Example 2 (600 g) were charged into a fluid bed coater. The Opadry AMB coating solution was sprayed onto the pellets with a product temperature at 39° C. until 3% weight gain was reached to yield an Opadry AMB-coated immediate release core.

Example 4

Barrier Coats of the Immediate Release Core

Ethylcellulose Coating Solution:

| | |
|---|---|
| Ethylcellulose | 73.9 g |
| PVP K90 | 1.72 g |
| Triethyl citrate | 8.1 g |
| Isopropyl alcohol | 1000 g |
| Ethyl alcohol | 1000 g |

Uncoated pellets from Example 2 (600 g) were charged into a fluid bed coater. The ethylcellulose coating solution was sprayed onto the pellets with a product temperature at 35° C. until 3%, 6% or 9.2% weight gain was reached to yield the EC-coated immediate release core.

For a slower release core, PVP K90 is used at lower levels or can be omitted.

Example 5

Neutralizing Agent-Containing Barrier Coats of the Immediate Release Core

Neutralizing Agent-Containing Barrier Coat Solution:

| | |
|---|---|
| Opadry White | 30 g |
| Malic acid | 30 g |
| Deionized water | 540 g |

The 3% Opadry AMB-coated pellets (Example 3) were further coated with the neutralizing agent-containing barrier coat solution to 10% weight gain. An additional coat of Opadry AMB was also applied to some of the resultant pellets.

Example 6 pH Sensitive Enteric Release Coatings

| Enteric coating solution 1 (Duodenum): | |
|---|---|
| Eudragit L 30 D-55 | 840 g |
| Triethyl citrate | 12 g |
| Talc | 24 g |
| Deionized water | 324 g |
| Enteric coating solution 2 (Jejunum): | |
| Eudragit L100 | 390 g |
| Talc | 24 g |
| Triethyl citrate | 34 g |
| Isopropyl alcohol | 2460 g |
| Acetone | 377 g |
| Deionized water | 390 g |
| Enteric coating solution 3 (Colon): | |
| Eudragit FS 30 D | 540 g |
| Triethyl citrate | 9 g |

| | |
|---|---|
| Talc | 45 g |
| Deionized water | 304 g |

(a) The ethylcellulose (EC)-coated immediate release core from Example 4 was further coated with enteric coating solution (1) to 40%, 45% or 50% weight gains to yield the duodenum-targeting particles.

(b) The EC-coated immediate release core from Example 4 was further coated with enteric coating solution (2) to 40%, 45%, 50%, or 60% weight gain to yield the jejunum-targeting particles.

(c) The Opadry AMB coated immediate release core from Example 3 was further coated with enteric coating solution (3) to 40%, 45% or 50% weight gain to yield the colon-targeting particles.

(d) The core coated with neutralizing agent-containing barrier coats from Example 5 was coated with an additional coat with enteric coating solution (3) to 40%, 45% or 50% weight gain to yield the colon-targeting particles.

Example 7

Figure 2:
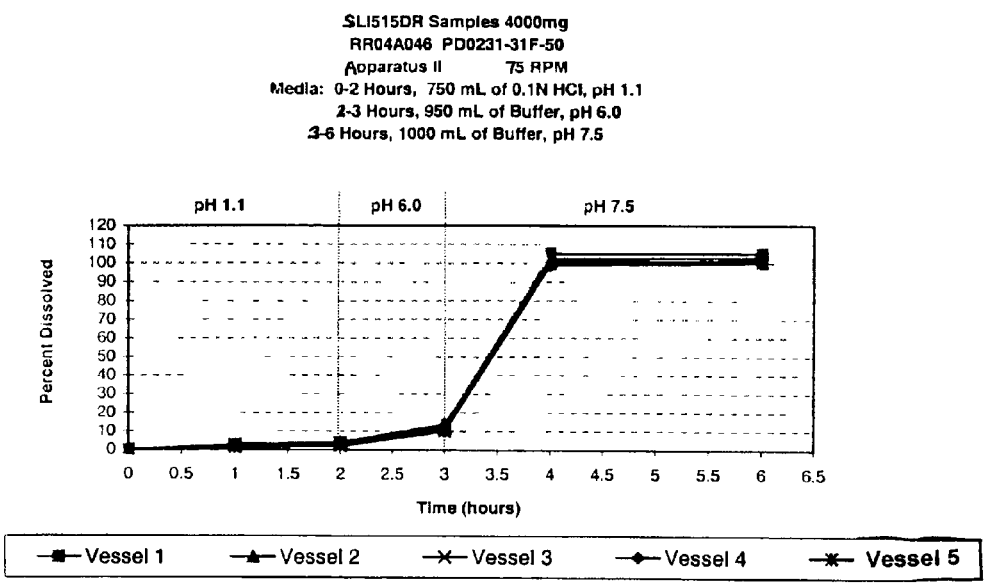
FIG. 2. Dissolution profile of a colon-targeting delayed release prototype without a neutralizing agent in the barrier coat.
Figure 3:
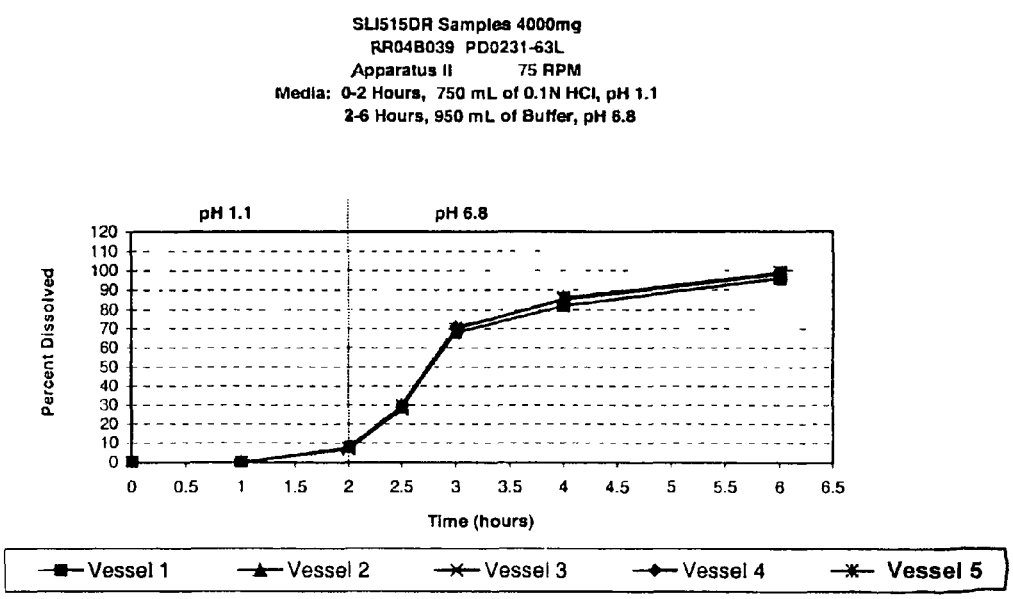
FIG. 3. Dissolution profile of a duodenum-targeting delayed release prototype without a neutralizing agent in the barrier coat.
Figure 4:
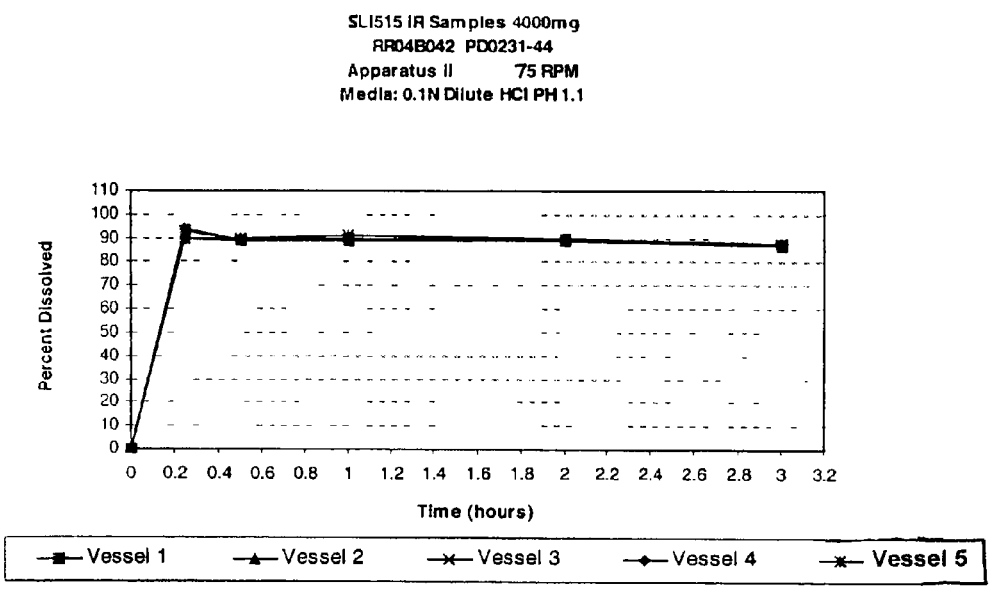
FIG. 4. Dissolution profile of an immediate release core of the present invention.
Figure 5:
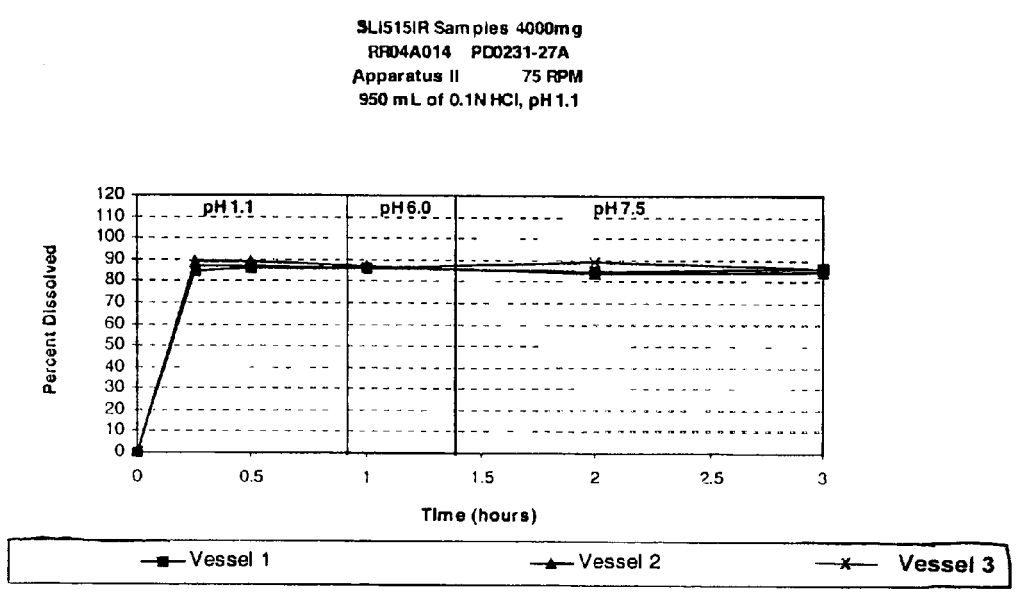
FIG. 5. Dissolution profile of an Opadry AMB-coated immediate release core of the present invention.
Figure 6:
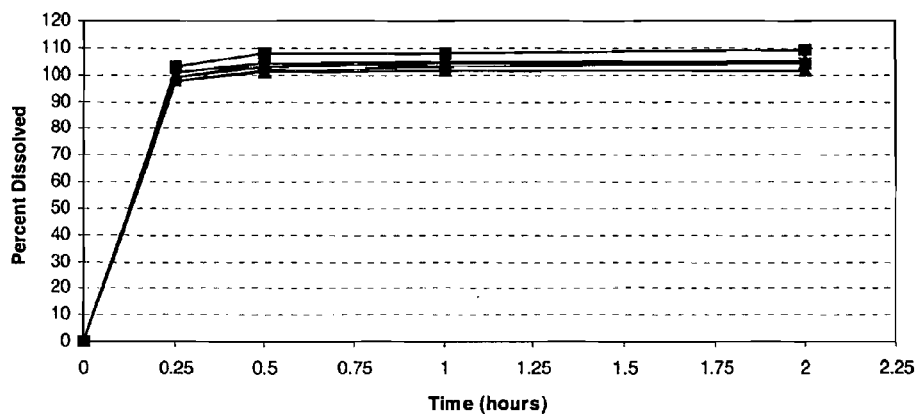
FIG. 6. Dissolution profile of an ethylcellulose-coated immediate release core of the present invention.

Dissolution Profiles of Various Prototypes—Gastro-Stability Improvement by the Neutralizing Agent in the Barrier Coats Delayed/Controlled Release Prototypes Colon-targeting prototype having a neutralizing agent (malic acid) in the barrier coat (PD0231-26B-50) does not release any sodium gamma-hydroxybutyrate at pH 1.1 and pH 6.0 for up to 3 hours (FIG. 1), whereas the one without the neutralizing agent in the barrier coat (PD0231-31F-50) releases 3% at pH 1.1 in 2 hours and 12% at pH 6.0 in 1 hour (FIG. 2). The neutralizing agent in the barrier coats thus improves the gastro-stability of the prototypes significantly.

Immediate Release Prototypes

Immediate release core (PD031-44), Opadry AMB-coated immediate release core (PD0231-27A) and an EC-barrier coated immediate release core (PD0231-38E) all showed an immediate release profile at pH 1.1.

Example 8

Canine PK Study

Four prototypes were used in the cross-over dog PK study, including an immediate release core (as the immediate release component in the current invention, IR) (see Ex. 2), an Eudragit L 30 D-55 coated delayed release prototype (DR2) (see Ex. 6a), an Eudragit FS 30 D coated delayed release prototype (DR1-no acid) (see Ex. 6c) and an Eudragit FS 30 D coated delayed release prototype with malic acid as the neutralizing agent in the barrier coats (DR1—with acid) (see Ex. 6d). A total of 6 dogs (3 males and 3 females) were given two oral capsules of one of the prototypes containing 1 g of sodium gamma-hydroxybutyrate per capsule. There was a minimum of a 2-day washout between each dose. Blood was collected at the following time points: 0 (pre-dose), 0.5, 1, 2, 3, 4, 5, 6, 7, 8, 10, 12, and 14 Hrs post dose (for a total of 312 samples). Plasma samples were analyzed using a verified LC/MS/MS method. Relative bioavailability was determined by comparing the AUC from the delayed release prototype group to the AUC of the immediate release prototype group.

The results show that the lower in the GI, the lower the bioavailability (BA); i.e., absorption is higher at upper GI.

Figure 7:
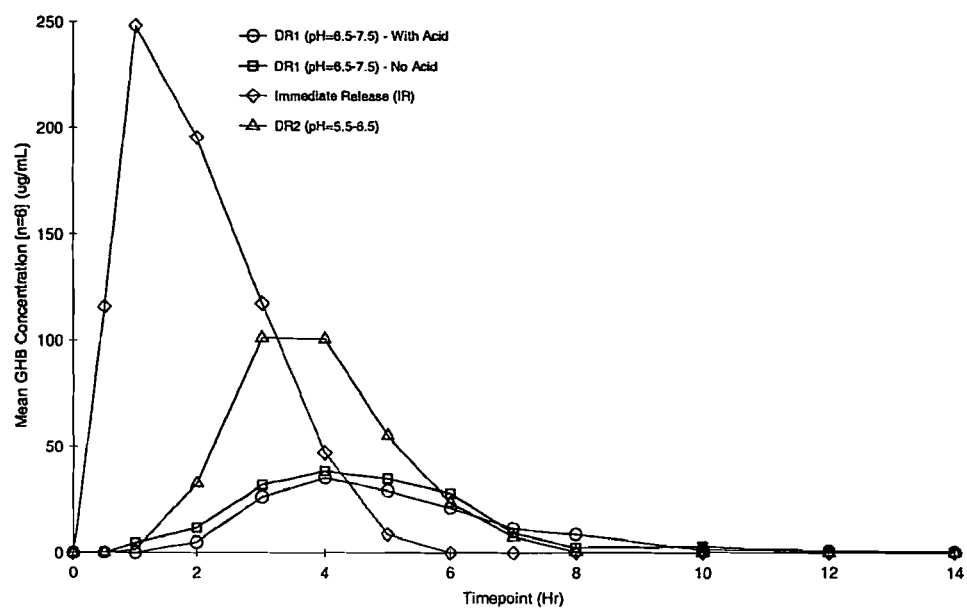
FIG. 7. Dog pharmacokinetic profiles—demonstrating region of absorption.

The immediate release component has the highest BA, so GHB may be absorbed better in its acid form. The BAs for the delayed release components with or without a neutralizer in the barrier coat do not vary much, so the neutralizer helps the coating—in turn the gastro-stability—but does not affect the BA. See Table 3 and FIG. 7.

TABLE 3

Mean GHB Concentrations (ug/mL)

| Time Point (Hr) | Period 1 DR1-w/Acid | Period 2 DR1-No Acid | Period 3 IR | Period 4 DR2 |
|---|---|---|---|---|
| 0 | 0.00 | 0.00 | 0.00 | 0.00 |
| 0.5 | 0.00 | 0.00 | 116.04 | 0.00 |
| 1 | 0.00 | 4.76 | 248.27 | 1.53 |
| 2 | 4.99 | 11.62 | 195.51 | 32.52 |
| 3 | 26.31 | 31.88 | 117.56 | 100.99 |
| 4 | 35.14 | 38.26 | 47.21 | 100.57 |
| 5 | 29.18 | 34.77 | 8.74 | 54.99 |
| 6 | 21.09 | 27.83 | 0.00 | 23.42 |
| 7 | 11.25 | 9.13 | 0.00 | 7.52 |
| 8 | 8.67 | 2.53 | 0.00 | 0.34 |
| 10 | 1.43 | 3.03 | 0.00 | 0.00 |
| 12 | 0.98 | 0.67 | 0.00 | 0.00 |
| 14 | 0.43 | 0.00 | 0.00 | 0.00 |
| Tmax (Hr) | 4.2 | 5.2 | 1.2 | 3.7 |
| Cmax (ug/mL) | 38.77 | 58.44 | 249.5 | 112.7 |
| AUClast | 134.3 | 162.6 | 601.0 | 318.4 |
| Rel BA | 22% | 27% | 100% | 53% |

What is claimed is:

1. A once-daily oral pharmaceutical dosage form, comprising:
   (a) a solid immediate release component comprising a gamma-hydroxybutyric acid (GHB) salt,
   (b) a first delayed release component comprising the GHB salt, and
   (c) a second delayed release component comprising the GHB salt,
   wherein the first delayed release component releases GHB in the duodenum and comprises a GHB containing core surrounded by a barrier coat, which in turn is surrounded by an enteric coating comprising a pH sensitive material that dissolves in the duodenum, and
   wherein the second delayed release component releases GHB in the colon and comprises a GHB containing core surrounded by a barrier coat, which in turn is surrounded by a coating comprising a pH sensitive material that dissolves in the colon.

2. The oral dosage form of claim 1, wherein said barrier coat contains a neutralizing agent or agents selected from the group consisting of malic acid, citric acid, tartaric acid, ascorbic acid, oleic acid, capric acid, caprylic acid, benzoic acid, a polyacid, and acidic ionic resins.

3. The oral dosage form of claim 2, wherein the neutralizing agent(s) are used in amounts sufficient to neutralize any migrating gamma-hydroxybutyric acid salts.

4. The oral dosage form of claim 3, wherein said neutralizing agent(s) are used in an amount of about 0.01% to about 10% mol/mol of the GHB.

5. The oral dosage form of claim 4, wherein the amount is from about 1% to about 5% mol/mol of the GHB.

6. The oral dosage form of claim 1, wherein the barrier coat is composed of materials selected from the group consisting of ethylcellulose, methylcellulose, hydroxypropyl cellulose, hydroxypropyl methylcellulose, cellulose acetate, cellulose acetate phthalate, and polyvinyl alcohol.

7. The oral dosage form of claim 1, wherein the core is surrounded by more than one barrier coat.

8. The oral dosage form of claim 7, wherein a first barrier coat comprises polyvinyl alcohol, a second barrier coat comprises ethylcellulose, and a third barrier coat comprises hydroxypropylmethylcellulose.

9. The oral dosage form of claim 1, wherein the enteric coating comprises methacrylate-based coating materials, cellulose-based coating materials, shellac-based coating materials, polyvinyl acetate phthalate, or combinations thereof.

10. The oral dosage form of claim 9, wherein the cellulose-based coating materials are selected from the group consisting of cellulose acetate phthalate, carboxymethyl ethylcellulose, cellulose acetate trimellitate, hydroxypropylmethylcellulose phthalate, and hydroxypropylmethylcellulose acetate succinate.

11. The oral dosage form of claim 1, wherein the core further comprises one or more excipients selected from the group consisting of binders, lubricants, anti-adherents, glidants and neutralizing agents.

12. The oral dosage form of claim 9, wherein the enteric coating further comprises acidic materials that counteract the alkaline effects of GHB.

13. An oral pharmaceutical dosage form, comprising:
   (a) a solid immediate release component comprising a gamma-hydroxybutyric acid (GHB) salt,
   (b) a first delayed release component comprising the GHB salt, and
   (c) a second delayed release component comprising the GHB salt,
   wherein the first delayed release component releases GHB in the duodenum and comprises a GHB containing core surrounded by a barrier coat, which in turn is surrounded by an enteric coating comprising a pH sensitive material that dissolves in the duodenum, and
   wherein the second delayed release component releases GHB in the colon and comprises a GHB containing core surrounded by a barrier coat, which in turn is surrounded by a coating comprising a pH sensitive material that dissolves in the colon.

14. A method for the treatment of a subject in need of the effects of GHB, comprising administering an effective amount of the oral dosage form of claim 1 to the subject.

15. The method of claim 14, wherein the subject is a human.

* * * * *